(12) United States Patent
Nieuwenhuis et al.

(10) Patent No.: US 8,283,912 B2
(45) Date of Patent: Oct. 9, 2012

(54) SENSOR DEVICE WITH MAGNETIC WASHING MEANS

(75) Inventors: Jeroen Hans Nieuwenhuis, Waalre (NL); Petrus Johannes Wilhelmus Van Lankvelt, Boekel (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 368 days.

(21) Appl. No.: 12/593,735

(22) PCT Filed: Mar. 31, 2008

(86) PCT No.: PCT/IB2008/051200
§ 371 (c)(1),
(2), (4) Date: Sep. 29, 2009

(87) PCT Pub. No.: WO2008/120169
PCT Pub. Date: Oct. 9, 2008

(65) Prior Publication Data
US 2010/0060265 A1    Mar. 11, 2010

(30) Foreign Application Priority Data
Apr. 3, 2007   (EP) ..................................... 07105564

(51) Int. Cl.
*G01N 27/74* (2006.01)
(52) U.S. Cl. ................. 324/204; 435/5; 435/6; 435/7.1; 436/519; 436/526
(58) Field of Classification Search .................... 324/204
See application file for complete search history.

(56) References Cited

U.S. PATENT DOCUMENTS

| | | | | |
|---|---|---|---|---|
| 5,252,493 A * | 10/1993 | Fujiwara et al. | ............... | 436/526 |
| 6,084,399 A * | 7/2000 | Nagaishi et al. | ............... | 324/204 |
| 6,597,176 B2 * | 7/2003 | Simmonds et al. | ........... | 324/326 |
| 7,749,445 B2 * | 7/2010 | Masters | ..................... | 422/82.01 |
| 2002/0135358 A1 * | 9/2002 | Sager et al. | ................... | 324/204 |
| 2004/0033627 A1 | 2/2004 | Aytur et al. | | |
| 2004/0077105 A1 | 4/2004 | Wu et al. | | |
| 2005/0069923 A1 * | 3/2005 | Mullis et al. | ...................... | 435/6 |
| 2006/0269966 A1 * | 11/2006 | Miyamoto et al. | ............. | 435/7.1 |
| 2007/0116602 A1 * | 5/2007 | Lee | ........................... | 422/82.01 |
| 2007/0190662 A1 * | 8/2007 | Baetzold et al. | ............. | 436/166 |
| 2007/0281288 A1 * | 12/2007 | Belkin et al. | ...................... | 435/4 |
| 2007/0281369 A1 * | 12/2007 | Carter et al. | .................. | 436/518 |
| 2008/0193967 A1 * | 8/2008 | Bommarito et al. | ........... | 435/34 |
| 2008/0262321 A1 * | 10/2008 | Erad et al. | ..................... | 600/301 |
| 2008/0314749 A1 * | 12/2008 | Johnson et al. | ............... | 204/450 |
| 2009/0170065 A1 * | 7/2009 | Wirix-Speetjens et al. | ...... | 435/5 |

FOREIGN PATENT DOCUMENTS

| EP | 1890157 A1 | 2/2008 |
|---|---|---|
| WO | 9322678 A2 | 11/1993 |
| WO | 03054523 A2 | 7/2003 |
| WO | 03054566 A1 | 7/2003 |
| WO | 2005010542 A1 | 2/2005 |
| WO | 2005010542 A2 | 2/2005 |
| WO | 2005010543 A1 | 2/2005 |

(Continued)

*Primary Examiner* — Timothy J Dole
*Assistant Examiner* — Benjamin M Baldridge

(57) ABSTRACT

A sensor device for detecting magnetic particles in a sensitive region of a sample chamber includes a dump region. Magnetic particles can be moved by magnetic forces from the sensitive region into the dump region which is arranged such that the magnetic particles cannot return to the sensitive region by pure sedimentation. The separation between the sensitive and the dump region can optionally be enforced by a barrier.

9 Claims, 3 Drawing Sheets

FOREIGN PATENT DOCUMENTS

| | | |
|---|---|---|
| WO | 2005038911 A1 | 4/2005 |
| WO | 2006059270 A2 | 6/2006 |
| WO | 2007129275 A2 | 11/2007 |
| WO | 2008075285 A1 | 6/2008 |

* cited by examiner

SENSOR DEVICE WITH MAGNETIC WASHING MEANS

The invention relates to a method and a microelectronic sensor device for the detection of magnetic particles in a sensitive region of a sample chamber, wherein unbound particles can be washed away from said region.

From the WO 2005/010543 A1 and WO 2005/010542 A2, a microelectronic sensor device is known which may for example be used in a microfluidic biosensor for the detection of molecules, e.g. biological molecules, labeled with magnetic beads. Furthermore, the US 2004/0033627 A1 describes the use of an external magnetic field for magnetic washing, i.e. the removal of unbound magnetic particles from a sensor surface. A problem of such an approach is however that the applied magnetic fields usually disturb the measurements of the sensor device in various ways.

Based on this situation it was an object of the present invention to provide means that allow an accurate detection of magnetic particles in a sensor region with minimized disturbances due to unbound magnetic particles and/or the process of their removal.

The microelectronic sensor device according to the invention serves for the detection of magnetic particles, which are usually nanometer-sized particles that can be magnetized when they are exposed to a magnetic excitation field. The magnetic particles are often used as labels for target components like biomolecules one is actually interested in. The sensor device comprises the following components:

a) A "sample chamber" in which a fluid containing the magnetic particles to be detected can be provided. The sample chamber is typically an empty cavity or a cavity filled with some substance like a gel that may absorb a sample; it may be an open cavity, a closed cavity, or a cavity connected to other cavities by fluid connection channels.

b) At least one sensor element for detecting magnetic particles in an associated sub-region of the sample chamber located at the bottom of the sample chamber, wherein this sub-region is called "sensitive region" in the following. In this context, the term "bottom" refers to an operating position with a certain orientation of the sensor device with respect to the gravitational field which is (or can be) assumed by the device during its application. The "bottom" of the sample chamber is in this operation position that part of the chamber surface where masses inside the sample chamber will tend to move to under the influence of gravity, i.e. by sedimentation. The "sensitive region" usually comprises at least a part of this bottom surface and of the adjacent volume above it. It is typically identical to the volume of the sample chamber that is surveyed by the sensor element, i.e. a magnetic particle is detected by the sensor element if and only if it is inside the sensitive region.

Moreover, it should be noted that the bottom of the sample chamber is typically the surface of some substrate (e.g. a semiconductor material, glass, etc.) in which the sensor element and other microelectronic components are embedded.

c) A "magnetic manipulator", i.e. some device that can generate magnetic manipulation fields for moving magnetic particles from the aforementioned sensitive region to another, distinct sub-region of the sample chamber, which is called "dump region" in the following. The relation between sensitive region and dump region shall be such that, if the microelectronic sensor device is in its operating position with respect to the gravitational field, magnetic particles cannot reach the sensitive region from the dump region by sedimentation only, i.e. by moving under the pure influence of gravitational forces.

The described microelectronic sensor device has the advantage that magnetic particles can be removed from the sensitive region to some dump region where they are no longer in the reach of the sensor elements and from where they cannot move back to the sensitive region by sedimentation. Thus it is possible to keep the sensitive region free from removed magnetic particles for prolonged times even if the magnetic manipulation fields that have removed the particles have been switched off again. Measurements can therefore be made without disturbances by magnetic fields over comparatively long periods.

The detection of the magnetic particles in the sensitive region can be done with any suitable detection principle. Thus the device may for example comprise an optical, magnetic, mechanical, acoustic, thermal and/or electrical sensor element. A magnetic sensor element may particularly comprise a coil, Hall sensor, planar Hall sensor, flux gate sensor, SQUID (Superconducting Quantum Interference Device), magnetic resonance sensor, magneto-restrictive sensor, or magneto-resistive sensor of the kind described in the WO 2005/010543 A1 or WO 2005/010542 A2, especially a GMR (Giant Magneto Resistance), a TMR (Tunnel Magneto Resistance), or an AMR (Anisotropic Magneto Resistance). Optical, mechanical, acoustic, and thermal sensor concepts are described in the WO 93/22678, which is incorporated into the present text by reference.

In general, the relative arrangement of sensitive region and dump region may be arbitrary as long as magnetic particles cannot move from the dump region to the sensitive region by pure sedimentation. In a preferred embodiment, the dump region is disposed laterally of the sensitive region with respect to the direction of gravity. Particles can therefore not get from the dump region into the sensitive region under the pure influence of gravity (sedimentation).

In a further development of the invention, the microelectronic sensor device comprises a barrier element that is disposed in the sample chamber between the sensitive region and the dump region. The barrier element helps to prevent that magnetic particles can get from the dump region into the sensitive region, thus improving the qualitative and/or temporal effectiveness of the washing procedure. With the interposition of a barrier element, the dump region can optionally be arranged above the sensitive region. In the preferred lateral arrangement of the dump region with respect to the sensitive region, the barrier element hampers a return of magnetic particles into the sensitive region by processes like diffusion or Brownian motion. Thus the separation effect is improved and/or the distance between sensitive region and dump region can be reduced, allowing to arrange them immediately adjacent to each other.

A particularly important embodiment is achieved if the sensitive region comprises a surface with binding sites for magnetic particles (including the case of an indirect binding, i.e. that the magnetic particles are linked to some entities which can bind to the binding sites). The surface may for example be coated with antibodies that are specific to target molecules in the sample fluid which are labeled with magnetic beads. The removal of magnetic particles by the magnetic manipulation field can then be done in such a way that only unbound magnetic particles are affected, thus leaving in the sensitive region only (bound) magnetic particles one is actually interested in.

While the above description included the case that the microelectronic sensor device comprises just one sensor element with an associated sensitive region and dump region, it is preferred that the sensor device comprises a plurality of such sensor elements with associated sensitive regions and dump regions. The sensitive regions and/or dump regions of different sensor elements may overlap or even be completely identical in this case, though it is preferred that each sensor element has a sensitive region and/or a dump region of its own. The sensitive region and dump region of each sensor element may optionally constitute one cell or unit that it is repeated many times in e.g. a matrix arrangement.

The magnetic manipulator may be realized in many different ways as long as the required magnetic fields—particularly inhomogeneous magnetic fields with spatial field gradients—can be generated. In a preferred embodiment, the magnetic manipulator comprises at least one electromagnet that generates a gradient with a non-vertical component in the sensitive region. In this case the magnetic particles can be pulled in a sideward direction away from the sensitive region, such that the sedimentation that is directed vertically downwards will not bring them back into the sensitive region.

In a further development of the invention, the microelectronic sensor device comprises a storage region at the top of the sample chamber for storing and selectively releasing magnetic particles. The top of the sample chamber is in this context again defined with respect to the usual operating position of the device in the gravitational field and may particularly lie vertically above the bottom of the sample chamber. Storing magnetic particles at the top of the sample chamber has the advantage that they can be released from there at the beginning of an assay and will then migrate under the influence of gravity through the sample fluid towards the sensitive region, thus coming into good contact with the whole sample fluid.

The invention further relates to a method for the detection of magnetic particles which comprises the following steps:
 a) Providing in a sample chamber a sample fluid that contains the magnetic particles to be detected.
 b) Moving magnetic particles with the help of magnetic manipulation forces from a sensitive region at the bottom of the sample chamber to a dump region of the sample chamber, wherein magnetic particles cannot reach the sensitive region from the dump region by sedimentation.
 c) Detecting magnetic particles in the sensitive region, for example by detecting magnetic stray fields that are generated by these particles.

The method comprises in general form the steps that can be executed with a microelectronic sensor device of the kind described above. Therefore, reference is made to the preceding description for more information on the details, advantages and improvements of that method.

In a preferred embodiment of the method, the time that is needed for the detection of the magnetic particles in steps c) is longer than the time that a magnetic particle needs (on average) to travel by sedimentation only a distance that is as long as the distance between sensitive region and dump region. If therefore a magnetic particle could freely move by sedimentation from the dump region to the sensitive region, it would reach the sensitive region before the measurements there would be completed. This scenario and the resulting disturbance of the measurement is however prevented by the required design of the sensitive region and the dump region, thus allowing comparatively long detection times (which are needed for sensitive measurements of low particle concentrations) and/or the use of large magnetic particles (which have a large sedimentation speed).

These and other aspects of the invention will be apparent from and elucidated with reference to the embodiment(s) described hereinafter. These embodiments will be described by way of example with the help of the accompanying drawings in which.

Like reference numbers or numbers differing by integer multiples of 100 refer in the Figures to identical or similar components.

Figure 1A:
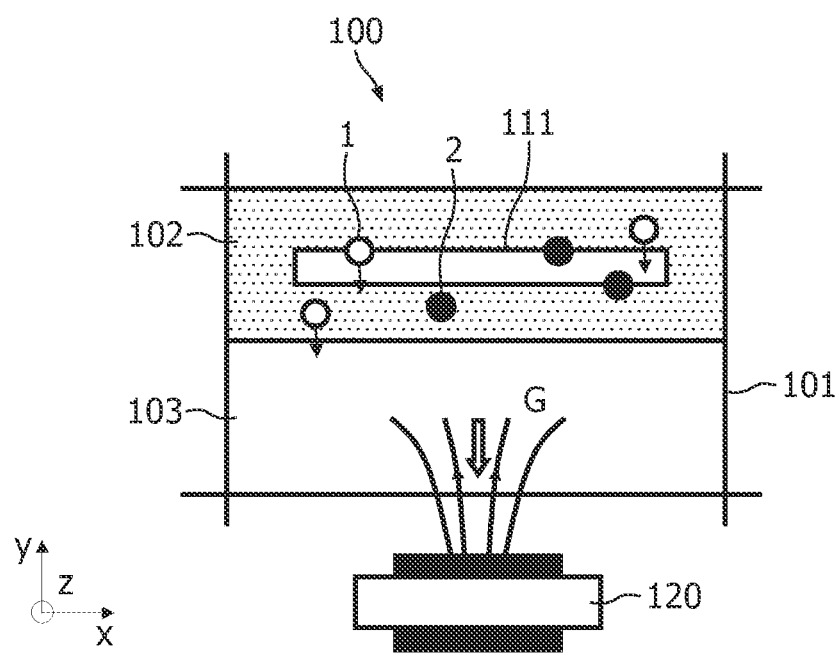
FIG. 1 shows in a schematic top view the magnetic washing (a) and the subsequent measurement (b) in a magnetic sensor device according to a first embodiment of the present invention.

Though the present invention can be applied to many kinds of microelectronic sensor devices that make for example use of optical or electrical detection principles, it will be described in the following with reference to magnetic sensor devices. Such magnetic sensor devices may particularly be applied as a biosensor for the detection of magnetically interactive particles, e.g. superparamagnetic beads, in a sample chamber. Magneto-resistive biochips or biosensors have promising properties for bio-molecular diagnostics, in terms of sensitivity, specificity, integration, ease of use, and costs. Examples of such biochips are described in the WO 2003/054566, WO 2003/054523, WO 2005/010542 A2, WO 2005/010543 A1, and WO 2005/038911 A1, which are incorporated into the present application by reference.

An important assay step in a (e.g. magnetic) biosensor is the so-called stringency step, in which a distinction is made between signals due to weak and due to strong biochemical bindings. In such a step, the bound materials are put under stress and tested for the strength and specificity of their binding. In state-of-the-art systems, stringency is usually applied by a washing step at the endpoint of the assay. This step cannot easily be transferred to a rapid and cost-effective biosensor, because the method requires a washing solution and mechanical pumping or valving.

Besides sensitivity, speed is also important for an assay. In a high-speed biosensor system (e.g. drugs-of-abuse testing in saliva), the kinetics of the binding process may be analyzed in order to perform a rapid measurement. Therefore, the washing step should be easily repeatable.

An assay of the kind described above is typically carried out in a sample chamber, where the sensor is located at the bottom of the chamber. During the assay the magnetic beads need to have sufficient interaction with the sample and they need to end up near the sensor surface. For this reason it is favorable to store the magnetic beads near the top of the sample chamber and to let them settle or to actively pull them down towards the sensor surface during the measurement. In this way the beads can move through the entire volume of sample liquid to guarantee good sample interaction.

Thus in a typical assay all of the magnetic particles need to be moved towards the sensor surface during a first phase. Next the beads can interact with the sensor surface and some of the beads will bind at the sensor surface. Finally, the beads that did not get a chance to bind at the sensor surface need to be washed away. They need to be moved far enough from the sensor so that they do not give rise to a sensor signal. If this is done by magnetic forces pulling the beads vertically upwards away from the sensor surface, there are at least two situations where this causes problems:

Typically it is not possible to perform magnetic washing and reading out of the sensor at the same time. Therefore, first the beads are pulled upwards, then the magnetic washing is switched off and the sensor reading can start to determine how many bound particles remain at the sensor. When large beads and/or large measurement times are used, the beads may settle back into the sensitive region of the sensor during the reading. This gives rise to erroneous signals.

When the sample chamber is very shallow, the non-bound beads will still give a signal, even if they are pulled against the top of the sample chamber. A shallow sample chamber may for example be necessary as a consequence of the fabrication technology.

In order to address these issues, it is proposed here to not only move the magnetic particles vertically during magnetic washing, but to move them also laterally. More generally speaking, the magnetic particles are brought during magnetic washing from a "sensitive region" into a "dump region" from where they cannot return to the sensitive region by pure sedimentation.

FIG. 1 shows in a top view a principal sketch of a magnetic sensor device 100 that realizes the aforementioned general approach. The magnetic sensor device 100 comprises the following components:

A sample chamber 101 which extends into the space above the drawing plane and in which a sample fluid with magnetic beads 1, 2 can be provided.

A magnetic sensor element comprising for example a GMR element 111 for detecting magnetic stray fields B' of magnetic particles 2 in its vicinity.

A sensitive region 102 that comprises a part of the bottom of the sample chamber 101 and at least a part of the volume above it, wherein said sensitive region is defined as the space of the sample chamber in which the signal of magnetic particles that is generated in the magnetic sensor element 111 is above a given threshold of detection. The bottom surface of the sample chamber 101 is typically coated with binding sites within the sensitive region 102 such that target molecules labeled with magnetic beads 1, 2 can specifically bind to them. In the Figure, magnetic beads that are bound to binding sites are drawn in black and indicated with the reference number 2, while unbound magnetic particles are open circles and carry the reference number 1.

A dump region 103 that is a sub-region of the sample chamber 101 distinct from the sensitive region. In the shown magnetic sensor device 100, the dump region 103 comprises the bottom surface of the sample chamber 101 immediately adjacent to the sensitive region 102 and at least a part of the space above it.

A magnetic manipulator, realized for example by an external electromagnet 120, that can generate a magnetic manipulation field within the sample chamber 101. The magnetic manipulation field has a field gradient G with at least a component in lateral direction, i.e. perpendicular to the vertical axis (z-axis in the Figure) that is defined by gravity.

As is indicated in the Figure, the magnetic sensor device 100 may typically comprise a plurality of units consisting of a sensitive and a dump region that are repeated in a matrix arrangement in a plane.

FIG. 1a) shows the magnetic sensor device 100 after the magnetic particles 1, 2 have collected in the sensitive region 102 due to sedimentation forces and optionally also assisted by magnetic attraction forces generated with additional magnets (not shown). As was already mentioned, some magnetic beads 2 have bound to binding sites in the sensitive region 102 while other magnetic beads 1 are unbound and free to move. Under the action of the magnetic gradient G, (only) the unbounded magnetic beads 1 start to move in lateral direction from the sensitive region 102 into the dump region 103.

Figure 1B:
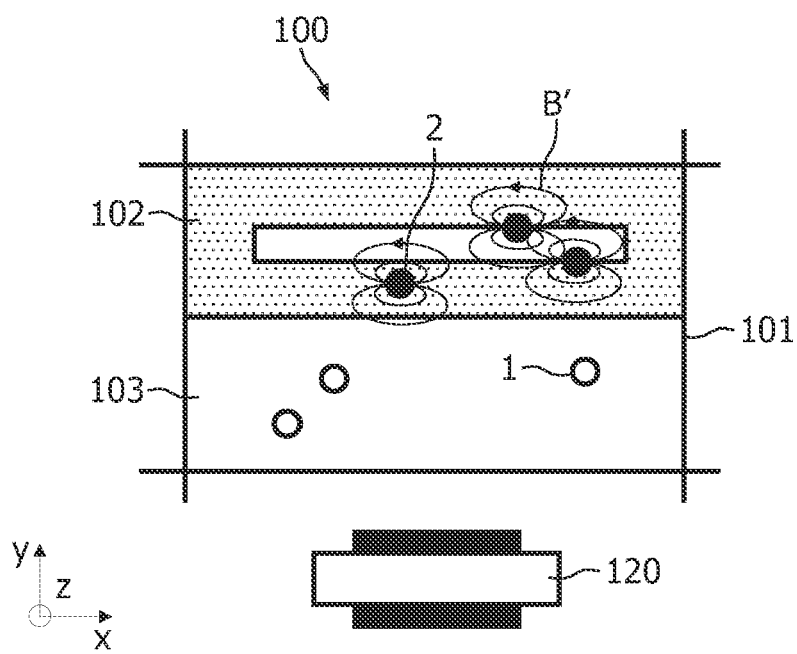

FIG. 1b) shows the device some time later, when all unbound magnetic particles 1 have collected in the dump region 103. Even though the manipulation magnet 120 is now switched off, the magnetic beads 1 will not return to the sensitive region as the dominant sedimentation force is directed vertically downward and thus does not lead into the sensitive region. The bound magnetic particles 2 in the sensitive region 102 can therefore be magnetized by magnetic excitation wires (not shown), and their stray fields B' can be measured by the magnetic sensor element 111 without disturbances from (i) the magnetic manipulation field or (ii) returning unbound beads 2.

The advantages of the described design are multiple:

When the beads 1 are also moved laterally during magnetic washing, they do not fall back towards the sensor surface as soon as the magnetic washing field is switched off. They can only return to the sensor by diffusion/Brownian motion. Especially for larger beads (>300 nm) where sedimentation starts to become a problem, the diffusion is typically quite slow. So, even in shallow sample chambers it is allowed to perform long measurements without being hindered by non-bound beads 1 coming back into the sensitive region.

Magnetic washing can also be used when the sample chamber is so shallow that even when the particles are moved against the ceiling of the sample chamber they give still rise to a sensor signal. By moving them laterally far enough from the active sensor still good reading can be performed without interference from non-bound beads.

(Electro-)Magnets are parts that often can be used for other purposes, too, so no additional magnetic actuators are needed in theses cases to achieve lateral magnetic washing.

FIG. 2 shows in a side view a second embodiment of a magnetic sensor device 200 during four consecutive phases of the washing and measurement procedure. The sensor device 200 comprises the following components:

A sample chamber 201.

A magnetic sensor element with a GMR wire 211 disposed in a substrate beneath the bottom of the sample chamber 201, more particularly below a sensitive region 202 of the sample chamber.

Two magnetic excitation wires 212 arranged at both sides of the GMR element 211 for generating magnetic excitation fields within the sensitive region 102.

A dump region 203 that is located laterally of the sensitive region 202.

A magnetic manipulator in the form of an electromagnetic 220 that can generate a magnetic field gradient G which has at least a component in lateral direction (x-direction).

A wall or barrier 204 that extends upwards from the bottom of the sample chamber 201 between the sensitive region 202 and the dump region 203.

Figure 2A:
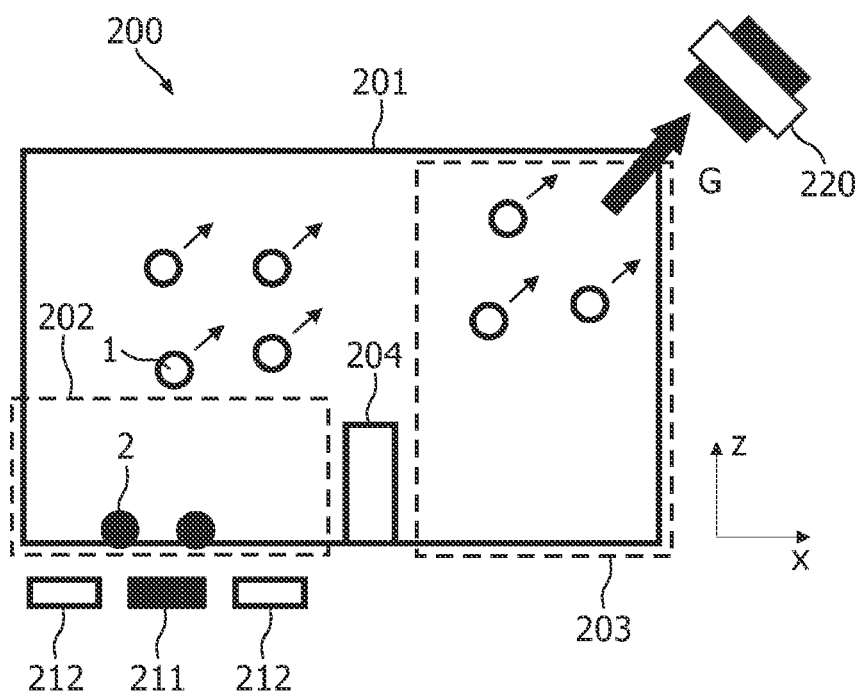
FIG. 2 shows in a schematic side view four consecutive steps of washing and measurement in a magnetic sensor device according to a second embodiment of the present invention, in which a barrier is disposed between the sensitive region and the dump region.

FIG. 2a) depicts the beginning of the washing, when unbound magnetic particles 1 are pulled away from the sensitive region 202 by the magnetic field gradient G generated by the electromagnetic 220.

Figure 2B:
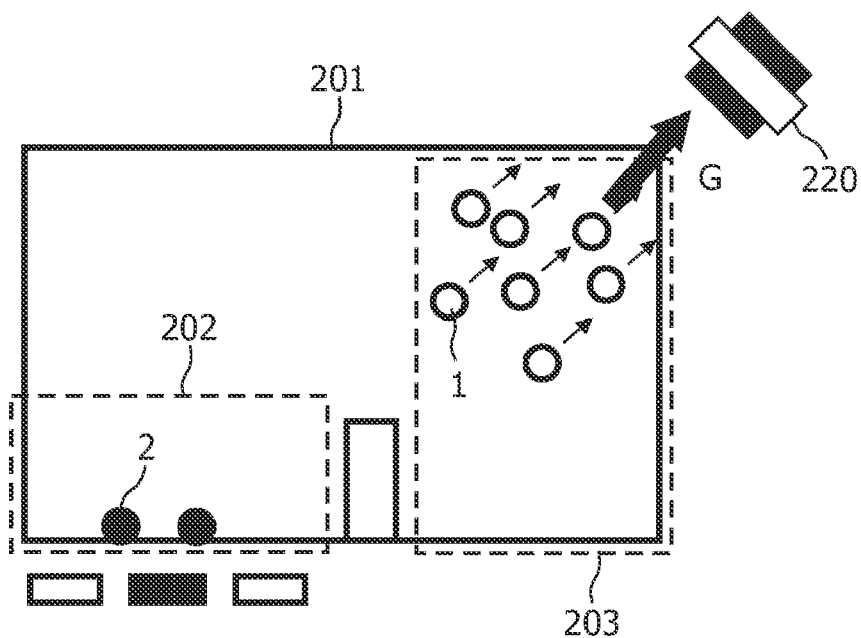

In the next FIG. 2b), all unbound magnetic particles 1 have collected in the upper right corner of the sample chamber 201, or, more precisely, of the dump region 203, while the bound magnetic particles 2 remained in the sensitive region 202.

Figure 2C:
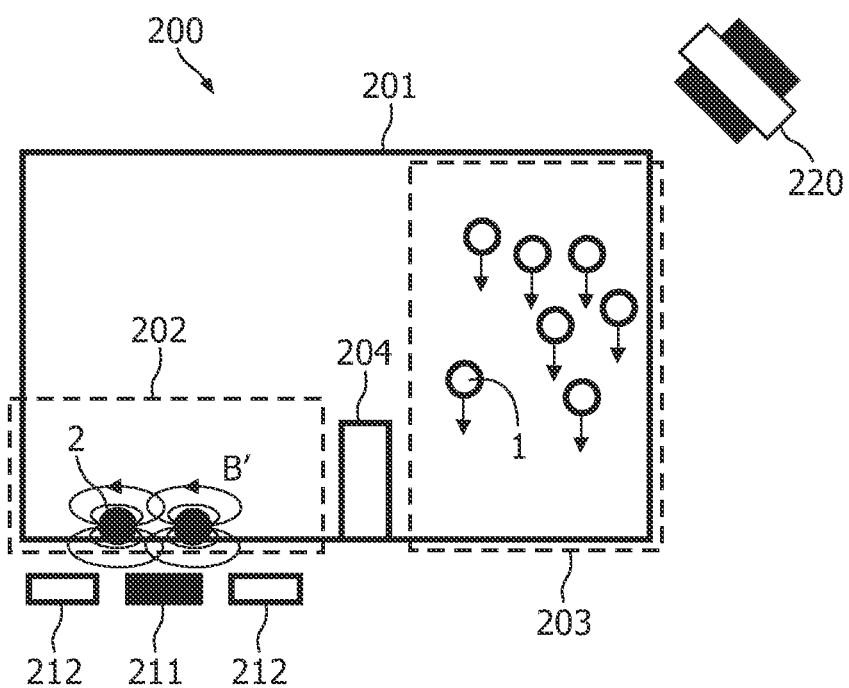

FIG. 2c) shows that the magnetic particles 1 in the dump region 203 settle to the bottom of this region after the electromagnet 220 has been switched off. The detection of the bound magnetic particles 2 in the sensitive region 202 has started by magnetizing them with the help of magnetic excitation fields (not shown) generated by the excitation wires 212; the resulting stray fields B' are then measured by the GRM element 211.

Figure 2D:
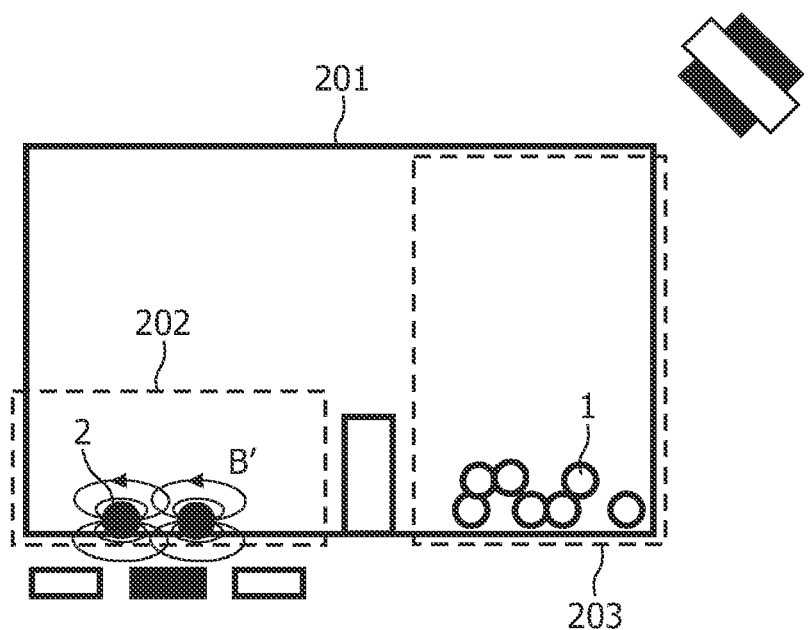

FIG. 2d) shows that after some time the unbound magnetic particles 1 have settled to the bottom of the dump region 203 such that the measurement in the sensitive region 202 can be continued unaffected.

In summary, the magnetic particles are moved diagonally away from the sensor surface towards a space for the unbound beads, by applying a vertical and a lateral magnetic field gradient at the same time. When the washing fields are switched off, the particles will not have a chance to move back towards the active sensor area, particularly if there is an additional barrier. This allows for arbitrarily long sensor read-out times.

The sensor devices disclosed here are particularly useful to detect very low concentrations of target molecules. In this operation range typically large beads are used to create sufficiently large sensor signals. These large beads tend to settle relatively quickly. Furthermore, to improve the signal-to-noise for measurements with a low bead concentration the sensor read-out time is typically large. The combination of fast sedimentation and the long measurement times (during which the beads can settle) gives rise to problems when only vertical washing is used. Those problems can be solved with the approach disclosed here.

While the invention was described above with reference to particular embodiments, various modifications and extensions are possible, for example:

The sensor can be any suitable sensor to detect the presence of magnetic particles on or near to a sensor surface, based on any property of the particles, e.g. it can detect via magnetic methods, optical methods (e.g. imaging, fluorescence, chemiluminescence, absorption, scattering, surface plasmon resonance, Raman, etc.), sonic detection (e.g. surface acoustic wave, bulk acoustic wave, cantilever, quartz crystal etc.), electrical detection (e.g. conduction, impedance, amperometric, redox cycling), etc.

The magnetic sensor can be any suitable sensor based on the detection of the magnetic properties of the particle on or near to a sensor surface, e.g. a coil, magneto-resistive sensor, magneto-restrictive sensor, Hall sensor, planar Hall sensor, flux gate sensor, SQUID, magnetic resonance sensor, etc.

In addition to molecular assays, also larger moieties can be detected with sensor devices according to the invention, e.g. cells, viruses, or fractions of cells or viruses, tissue extract, etc.

The detection can occur with or without scanning of the sensor element with respect to the sensor surface.

Measurement data can be derived as an end-point measurement, as well as by recording signals kinetically or intermittently.

The particles serving as labels can be detected directly by the sensing method. As well, the particles can be further processed prior to detection. An example of further processing is that materials are added or that the (bio) chemical or physical properties of the label are modified to facilitate detection.

The device and method can be used with several biochemical assay types, e.g. binding/unbinding assay, sandwich assay, competition assay, displacement assay, enzymatic assay, etc. It is especially suitable for DNA detection because large scale multiplexing is easily possible and different oligos can be spotted via ink jet printing on the optical substrate.

The device and method are suited for sensor multiplexing (i.e. the parallel use of different sensors and sensor surfaces), label multiplexing (i.e. the parallel use of different types of labels) and chamber multiplexing (i.e. the parallel use of different reaction chambers).

The device and method can be used as rapid, robust, and easy to use point-of-care biosensors for small sample volumes. The reaction chamber can be a disposable item to be used with a compact reader, containing the one or more field generating means and one or more detection means. Also, the device, methods and systems of the present invention can be used in automated high-throughput testing. In this case, the reaction chamber is e.g. a well-plate or cuvette, fitting into an automated instrument.

Finally it is pointed out that in the present application the term "comprising" does not exclude other elements or steps, that "a" or "an" does not exclude a plurality, and that a single processor or other unit may fulfill the functions of several means. The invention resides in each and every novel characteristic feature and each and every combination of characteristic features. Moreover, reference signs in the claims shall not be construed as limiting their scope.

The invention claimed is:

1. A microelectronic sensor device for the detection of magnetic particles comprising:
   a) a sample chamber in which a fluid containing the magnetic particles is provided;
   b) at least one sensor element that detects the magnetic particles in an associated sensing region at the bottom of the sample chamber;
   c) a magnetic manipulator that moves the magnetic particles from the sensing region to a dump region of the sample chamber, wherein
      the magnetic particles cannot reach the sensing region from the dump region by sedimentation, wherein the dump region is disposed laterally with respect to the sensing region, and wherein the sensor further comprises a barrier element that is disposed in the sample chamber between the sensing region and the dump region, and wherein
      the magnetic manipulator is positioned at a corner or side of the sample chamber and moves the magnetic particles diagonally away from the sensing region by simultaneously applying a vertical magnetic field and a lateral magnetic field gradient away from the sensing region.

2. The microelectronic sensor device according to claim 1, wherein the at least one sensor element comprises an optical, magnetic, mechanical, acoustic, thermal sensor or electrical sensor.

3. The microelectronic sensor device according to claim 2, wherein the sensor further comprises a coil, a Hall sensor, a planar Hall sensor, a flux gate sensor, a SQUID, a magnetic resonance sensor, a magneto-restrictive sensor, or a magneto-resistive sensor.

4. The microelectronic sensor device according to claim 1, wherein the sensing region comprises a surface with binding sites for magnetic particles.

5. The microelectronic sensor device according to claim 1, further comprising a plurality of sensor elements with associated sensing regions and dump regions.

6. The microelectronic sensor device according to claim 1, wherein the magnetic manipulator comprises an electromagnet that can generate a field gradient with a non-vertical component.

7. The microelectronic sensor device according to claim 1, further comprising a storage region at the top of the sample chamber for storing and selectively releasing magnetic particles.

8. A method for the detection of magnetic particles in a microelectronic sensor, comprising the following acts:
   a) providing a sample fluid containing the magnetic particles in a sample chamber of the microelectronic sensor;
   b) moving the magnetic particles with magnetic forces from a sensing region at the bottom of the sample chamber to a dump region disposed laterally with respect to the sensing region of the sample chamber, wherein the sensing region is separated from the dump region by a barrier element, and wherein magnetic particles cannot reach the sensing region from the dump region by sedimentation; and
   c) detecting magnetic particles in the sensing region, wherein the magnetic forces are generated by a magnetic manipulator positioned at a corner or wall of the sample chamber that moves the magnetic particles diagonally away from the sensing region by simultaneously applying a vertical magnetic field and a lateral magnetic field gradient away from the sensing region.

9. The method according to claim 8, wherein a time needed for the detection of at least one magnetic particle is longer than the time needed for at least one magnetic particle to travel by sedimentation a distance equal in length to the distance between the sensing region and the dump region.

* * * * *